(12) United States Patent
Kadioglu et al.

(10) Patent No.: US 7,162,373 B1
(45) Date of Patent: Jan. 9, 2007

(54) METHOD AND SYSTEM FOR ASSESSING LIFE OF CRACKED DOVETAIL IN TURBINE

(75) Inventors: Yavuz Kadioglu, Mechanicville, NY (US); Anil Kumar Gupta, Bangalore (IN); Ravichandran Pazhur Nair, Glenville, NY (US); Eric Joseph Ekland, Galway, NY (US); Eloy Vincent Emeterio, Amsterdam, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/282,691

(22) Filed: Nov. 21, 2005

(51) Int. Cl.
*G01B 5/30* (2006.01)
(52) U.S. Cl. .................................................. 702/35
(58) Field of Classification Search ............ 702/33–36, 702/179–181
See application file for complete search history.

(56) References Cited

U.S. PATENT DOCUMENTS

| | | | |
|---|---|---|---|
| 3,985,318 A | 10/1976 | Dominey et al. | 244/17.11 |
| 4,026,660 A | 5/1977 | Ueda et al. | 416/61 |
| 4,106,332 A | 8/1978 | McKeown | 73/104 |
| 4,502,331 A | 3/1985 | Singh et al. | 73/627 |
| 4,546,652 A | 10/1985 | Virkar et al. | 73/776 |
| 4,714,917 A | 12/1987 | Counter et al. | 340/679 |
| 4,875,170 A * | 10/1989 | Sakurai et al. | 702/34 |
| 5,952,836 A | 9/1999 | Haake | 324/718 |
| 5,969,260 A | 10/1999 | Belk et al. | 73/773 |
| 6,490,791 B1 | 12/2002 | Surace et al. | 29/889.1 |
| 6,732,591 B1 * | 5/2004 | Miles et al. | 73/808 |
| 6,756,908 B1 | 6/2004 | Gass et al. | 340/679 |
| 2002/0194733 A1 | 12/2002 | Surace et al. | 29/889.1 |
| 2003/0122682 A1 | 7/2003 | Gass et al. | 340/679 |

OTHER PUBLICATIONS

R.K. Nalla et al., "Mixed-Mode, High-Cycle Fatigue-Crack Growth Thresholds in Ti-6A1-4V: Role of Small Cracks", International Journal of Fatigue 24 (2002), 1047-1062.
"Stress Corrosion Cracking (SCC)", http://www.corrosion-doctors.org/Forms/scc.htm, printed Sep. 16, 2005, pp. 1-5.
"Stress Corrosion Cracking Mechanism", http://www.corrosion-doctors.org/Forms/scc-mechanism.htm, printed Sep. 16, 2005, pp. 1-2.
"Fracture Toughness", Knowledge Article from www.Key=to-Steel.com, printed Sep. 16, 2005, pp. 1-3.
Darryl A. Rosario et al., Development of An LP Rotor Rim-Attachment Cracking Life Assessment Code (LPRimLife), 6th EPRI Turbine/Generator Workshop, Aug. 17-20, 1999, St. Louis, MO, pp. 1-8.

* cited by examiner

*Primary Examiner*—Michael Nghiem
(74) *Attorney, Agent, or Firm*—Nixon & Vanderhye P.C.

(57) ABSTRACT

A method has been developed for predicting a remaining operational life of a turbine component including: obtaining crack flaw data regarding current crack flaws in the turbine component; using the crack flaw data with data regarding the structure and operating conditions of the turbine component to determine force loads applied to the turbine component and generate crack propagation data; applying a probalistic analysis to the crack flaw data and the generated crack propagation data to generate a statistical distribution of crack data, and applying the statistical distribution of crack data to predict a time to failure of the component by iteratively determining the force loads for successive periods of time.

20 Claims, 4 Drawing Sheets

METHOD AND SYSTEM FOR ASSESSING LIFE OF CRACKED DOVETAIL IN TURBINE

BACKGROUND OF THE INVENTION

This disclosure generally relates to steam turbines. More particularly, this disclosure relates to methods for assessing cracking of turbine rotors and other metal turbine components exposed to water, steam and condensate in the steam turbine.

Steam turbine power systems use a fluid medium such as water or another suitable chemical fluid with boiling points and latent heat values appropriate for the operational temperatures of the system. The fluid medium is generally heated in a separate heat source such as a boiler by using directed solar radiation, burning of fossil fuel, nuclear radiation or geothermal energy. The energy is transferred from the heat source to a turbine(s) in the form of high-pressure steam that powers the turbines. The steam turns a rotor in the turbine. The rotation of the turbine may be applied to drive an electromagnetic generator producing electricity.

A common type of steam turbine system includes a plurality of turbines in the form of a high-pressure turbine, an intermediate pressure turbine, and a low-pressure turbine. The turbines can be in a closed loop, which includes a steam generator for supplying steam to the high-pressure turbine and a condenser that receives the low-pressure turbine discharge. Water from the condenser is provided back to the heat source, e.g., steam generator, for reuse and is generally treated prior to reuse to remove impurities. The steam turbine extracts energy from the steam to power an electrical generator, which produces electrical power. Alternatively, low to medium pressure steam, after passing through the turbines, can be directed to an intermediate temperature steam distribution system, e.g., a heat exchanger, that delivers the steam to a desired industrial or commercial application such as is desired for combined heat and power applications.

As shown in FIG. 1, each turbine generally includes a fixed partition, e.g., nozzles, and a plurality of turbine buckets 10, e.g., blades, mounted on rotatable turbine wheels 12. The buckets are conventionally attached to the wheels by a dovetail 14. Dovetail attachment techniques between turbine buckets and turbine rotor wheels for steam turbines are well known in the art of steam turbines. The outer rim of the turbine wheel includes a tangential entry dovetail connector 16 having a circular ridges on opposite sides of the wheel to secure the buckets. The rim of the turbine wheel and bucket dovetails have generally complementary pine tree cross-sectional shapes.

Different types of dovetails may be employed. For example, finger-type and fir tree dovetails are used to secure the buckets and rotor wheel to one another. In a finger type of dovetail, the outer periphery of the rotor wheel has a plurality of axially spaced circumferentially extending stepped grooves for receiving complementary fingers on each of the bucket dovetails when the buckets are stacked about the rotor wheel. Pins are typically passed through registering openings of the dovetail fingers of each of the wheel and bucket dovetails to secure the buckets to the wheel. A fir tree dovetail connector includes a cutout for each bucket in the outer rim of the wheel. The cutouts may generally form a "V" and have ridges in their sides to secure a match dovetail in the bucket. A common difficulty with all types of dovetail configurations is that the dovetail connections between the buckets and wheels are highly stressed and, after years of operation, tend to wear out and crack.

Cracking of the various components in low-pressure turbines, such as at the dovetail connection, is believed to be related to a phenomena commonly referred to as stress corrosion cracking (SCC). Stress levels within the component can accelerate SCC. In particular, the stresses present in the hook fillet regions of typical dovetail configurations can accelerate SCC. Normally, these stresses are acceptable but with contaminated steam and age, cracks can initiate and, if left undetected, may grow to a depth that will cause failure of the wheel hooks. Moreover, the steam at the low-pressure end of the turbine, contaminated or otherwise, is at a lower temperature having been cooled during passage through the turbine. As a result, water condenses therefrom more readily and as a result, the steam at the low pressure end of the steam turbine is fairly saturated with water. Because of exposure to the steam, the transfer of energy by impact of the wet steam by itself on the turbine blades is greater at the low-pressure end of the turbine than that at the high-pressure end, resulting in greater stress applied to the turbine components.

The steam environment existing in the steam turbine considerably affects the rate of progress of SCC. As used herein, the term "steam environment" refers to an environment in which water droplets, water films, or capillary condensates exist. The reason for this is that chemical factors are involved in stress corrosion cracking so that stress corrosion cracking is promoted in certain specific temperature regions dependent on the relationship between the steam constituents and the chemical properties of the rotor material. Because of the mass and the rotational speed of a turbine, e.g., typically on the order of 3,600 revolutions per minute (rpm), significant damage to the turbine, its housing and surrounds, as well as injury to turbine operators, can occur should cracks develop in the wheel dovetail sufficiently to permit one or more of the buckets to fly off the rotor wheel. In extreme cases, all the hooks will fail and buckets will fly loose from the rotor. Long experience with bucket-to-wheel dovetail joints has generally indicated that the wheel hooks can crack through an SCC mechanism but that the bucket hooks typically do not crack through an SCC mechanism.

The duty cycle of a turbine is the operational schedule that states its operating steps and conditions, such as turbine inlet temperature, speed and output power; period at each power output level, and time between maintenance shutdowns.

The remaining life of a turbine dovetail is dependent on the amount of SCC and the rate at which it will progress over the life of the component and also the operating condition. The low-pressure (LP) sections of nuclear and fossil fuel driven steam turbines are especially susceptible to SCC. During periodic inspections, the amount of SCC is determined for each turbine rotor or for a representative sample of turbine rotor. Depending on the amount of SCC determined from the inspection, a decision is made as to whether to return the turbine to operation or to repair the turbine. This decision is typically made by a skilled technician or engineer who has inspected the cracks in the dovetails of the turbine buckets. Moreover, there is a need for such an analytical tool to assist in predicting the remaining life of cracked dovetails.

BRIEF DESCRIPTION OF THE INVENTION

There is a long felt need for an analytical tool to evaluate the impact that SCC will have on the useful life of a turbine rotor. It would be helpful to have such a tool when determining whether to return a turbine to service, or repair or replace the dovetail connectors on the wheels.

A method has been developed for predicting a remaining operational life of a turbine component comprising: obtaining crack flaw data regarding current crack flaws in the turbine component; using the crack flaw data with data regarding the structure and operating conditions of the turbine component to determine force loads applied to the turbine component and generate crack propagation data; applying a probalistic analysis to the crack flaw data and the generated crack propagation data to generate a statistical distribution of crack data, and applying the statistical distribution of crack data to predict a time to failure of the component by iteratively determining the force loads for successive periods of time.

A method has been developed for predicting a remaining operational life of a turbine component comprising: obtaining crack flaw data regarding current crack flaws in the turbine component; applying a probalistic analysis to the crack flaw data to generate statistical distributions of crack data and the propagation rate; using the crack flaw data distributions with data regarding the structure of the turbine component to determine loads applied to the turbine component; determining whether the turbine component has reached a crack failure criteria based on the crack flaw data and the determined loads, and determining crack propagation based on the crack flaw data and a period of elapsed operating time of the component, and applying adjusting the crack data to include the determined crack propagation.

A system has been developed for predicting a remaining operational life of a turbine component comprising: an inspection device that collects crack flaw data regarding current crack flaws in the turbine component; a computer system including a processor and a data storage device, wherein the data storage device stores the crack flaw data and data regarding the structure and operation of the turbine component and a software tool comprising algorithms for analyzing the software component and predicting a remaining life of the component; wherein the algorithms include a probalistic analytical tool receiving as inputs the crack flaw data and outputting a statistical distribution of crack data, and using the statistical distribution of crack flaw data and the data regarding the structure and operation of the turbine component to determine statistical distributions of force loads applied to the turbine component and statistical distributions of crack propagation resulting from the force loads, wherein the determination of force loads and crack propagation is performed iteratively to predict a time to failure of the component.

DETAILED DESCRIPTION OF THE INVENTION

Figure 2:
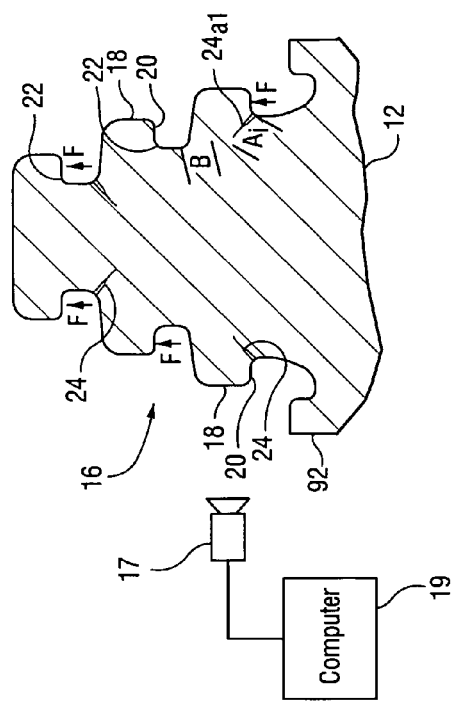
FIG. 2 is an enlarged cross-sectional view taken alone section 2—2 of FIG. 1 of a dovetail connector.
Figure 1:
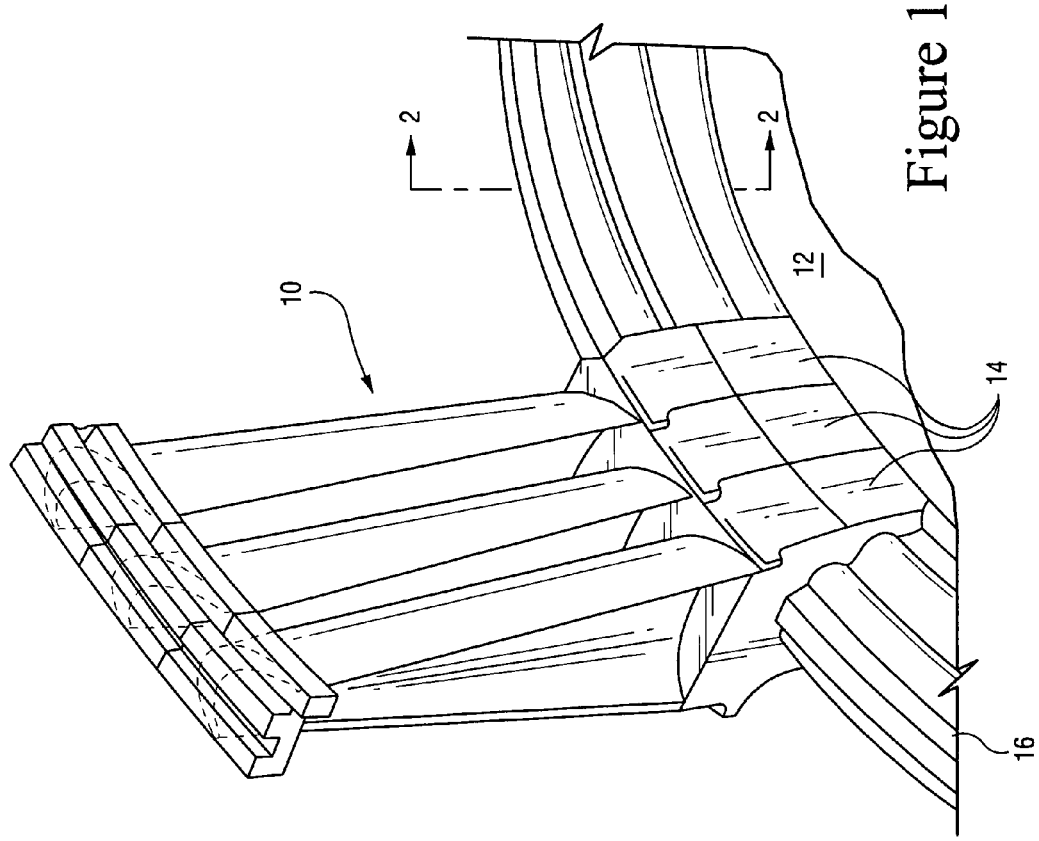
FIG. 1 is a perspective view of a portion of a steam turbine rotor having a dovetail connector at its perimeter and turbine buckets attached to the dovetail connector.

FIG. 2 is a cross-sectional diagram of a tangential dovetail connector 16 for a turbine wheel 12. The dovetail connector is at the outer circular rim of the wheel. The connector generally comprises a inverted "V" shape having a series of ridges 18 extending outwardly from the sides of the connector. These ridges 18 are generally referred to as "hooks" of the connector. The hooks provide an attachment for the matching dovetail 14 at the base of each turbine bucket 10.

The hooks 18 of the dovetail connector are generally loaded along their underside surfaces 20. The loading occurs as the matching hooks of the dovetail connector of the turbine bucket abut against the underside surfaces 20 of the dovetail connector on the wheel 12. During rotation of the wheel, centrifugal forces act in a radial direction. The centrifugal forces apply radial forces (F) to the underside surfaces 20 on the dovetail connector 16 of the wheel. These forces are proportional to the rotational speed of the wheel. The forces are generally constant as the steam turbine is typically operated at a relatively uniform rotational speed. However, the duty cycle of the steam turbine will cause periodic variations in the wheel velocity and includes certain shut down periods during which the wheel is stopped. The duty cycle for the turbine results in variations in the forces (F) applied to the hooks 18 of the dovetail connector on the wheel. Typically a steam turbine operates for weeks or months at a generally uniform rotational speed. The speed of the turbine varies as the turbine is shut down for inspection and maintenance and during certain other turbine operational procedures in which a turbine's operating speed is changed.

The forces (F) applied to the dovetail connector result in stresses applied to the connector. The distribution of forces applied to the dovetail connector 16 results in a concentration of stress at the fillets 22 between the hooks 18 and the other portions of the connector. The stresses at the fillets 22 can result in cracks 24 forming in the dovetail connector. The cracks are typically initiated where stress and corrosion are concentrated on the surface of the dovetail connectors, such as at the fillets. Corrosion may result from the steam passing through the turbine that partially seep between the dovetail connector of the turbine buckets and the dovetail connector of the wheel. The combination of stress and corrosion may cause the fillets 22 to become pitted. Pits in the fillets may become cracks 24 as the forces (F) act on the hooks 18.

The surfaces of the dovetail connector 16 are periodically inspected for cracks. Inspection occurs when the steam turbine is shut down. The dovetail connector 16 is carefully inspected to identify cracks 24 that have formed, especially at the fillets 22 of the connector. Ultrasonic surface inspection techniques are conventionally used to identify cracks 24 in a dovetail connector because this method of inspection does not require removal of the buckets, saving considerable cost and time. An ultrasonic inspection device 17 may be used to manually inspect the dovetail connector. These ultrasonic inspection techniques provide data regarding the location of cracks, the width of cracks, and in some instances, the expected depth (A) of a crack. This crack flaw data is carefully cataloged for a dovetail connector 16 during each inspection of the wheel. The crack flaw data is downloaded into a computer 19 that may have a processor and a data storage device to store the crack flaw data and data modeling the dovetail connection, and a software tool including algorithms for analyzing the crack flaw data and predicting an expected remaining life of the dovetail. The computer may be, for example, a personal computer or a network of computers where the storage of the modeling data for the dovetail is at a central location and the software tool and crack data at a computer workstation on the network.

The crack flaw data obtained during each inspection is applied to predict "remaining life" for the turbine wheel. The "remaining life" may be characterized as an operational period starting at the last wheel inspection in which maintenance, repair or replacement of the wheel is to be performed. The remaining life may be used by the turbine operator to determine when to schedule a time for maintenance, repair or replacement. The remaining life of the wheel is not a certain predictor of turbine wheel life or time to failure of the turbine wheel. Rather, it is an estimate based on the known current state of the cracks in the dovetail connector 16, and the expected operational duty cycle for the turbine.

Cracks 24 (a1, a2 and a3) tend to propagate into a dovetail. Stress and corrosion applied to the fillets 22 of the dovetail cause cracks to expand and increase in depth into the hooks 18 of the dovetail. The distance (A) as a function of operation time that a crack 24 propagates into a dovetail connector may be estimated using conventional mechanics and material algorithms. For example, applying conventional hook shear algorithms and knowing material strengths, the crack depth which will result in a hook 18 shearing off of a dovetail can be determined knowing the pressure, e.g., force over a surface 20 area, and the remaining area (B) of the material holding the hook 18 to the dovetail connector. The shearing of a hook 18 is one example of the failure of the turbine rotor. When a hook fails, the remaining hooks on the rotor are required to adsorb more of the centrifugal load and become more susceptible to failure. If the remaining hooks fail, the end bucket may become free and cause substantial damage to the rotor and turbine. Predicting the remaining life of the turbine wheel involves an analytical determination of when the dovetail connector is likely to fail, such as the shearing of a hook 18 due to crack propagation. Knowing the predicted remaining life of a turbine wheel, a turbine operator may schedule turbine wheel maintenance, repair or replacement so as to avoid turbine wheel failure.

Using conventional shear theory to predict the failure of a dovetail connector 16 is one means for predicting remaining life of the wheel. Other means for predicting the failure of a turbine wheel may be applied, including fracture mechanics approach and plastic limit load analysis. Accordingly, one or more of metal failure theories may be applied to estimate remaining life of a turbine wheel.

Figure 3:
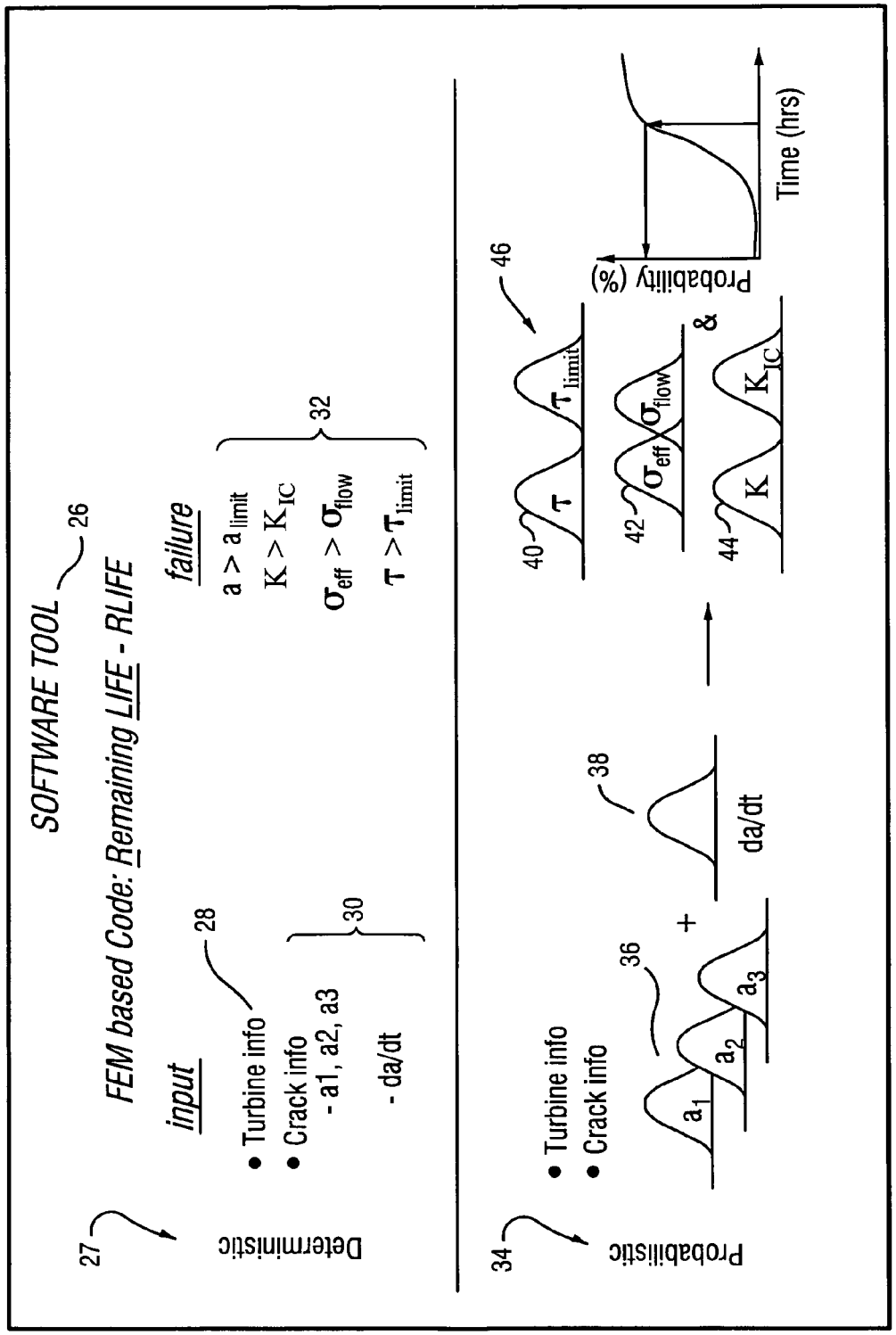
FIG. 3 is a block diagram of a software tool for predicting remaining life of a dovetail connector.

FIG. 3 is a high level schematic of the software remaining life prediction tool 26. The software program tool 26 predicts the remaining life of a turbine wheel. The tool 26 includes a deterministic engine 27 that predicts time to failure based on input data regarding turbine information and crack information. The inputs to the tool include data regarding the turbine 28 such as detailed digital models of the dovetail connector, e.g., a mathematical mesh model of the connector, and information regarding the turbine operating conditions, and the crack flaw data 30 from inspection(s) of the dovetail connector (e.g., crack width and/or depth for cracks a1, a2 and a3) and regarding the expected crack propagation rate (da/dt).

The prediction tool 26 receives as an input the detailed crack information obtained from the inspection of the turbine wheel. Each crack is identified during the inspection based on its location, width and/or depth. Further, crack propagation rates (da/dt) may be determined by comparing the crack inspection data from lab tests and previous successive wheel inspections. By inputting crack information to the prediction tool 26, the tool generates a predicted time to failure for the wheel. The crack propagation rate may be input as a known condition that is a constant or varies with other operating condition, such as temperature. For example, the crack propagation rate (da/dt) may predict that cracks grow at a certain rate per year for a given wheel temperature.

Including in the turbine data 28, a model of the dovetail is helpful in accurately calculating the hook loads. Using the hook loads, determinations may be made of the shear stress, plastic flow stress and stress intensity for a particular crack in a hook or combinations of cracks in the hook or hooks. Hook loads may be determined from a finite element (FE) analysis of the rotor dovetail.

Shear stress, plastic flow stress and stress intensity may be determined using small computer program scripts in the tool 26. Manufactures of turbine typically have mathematical models of turbine components, e.g., wheels, that are used for the manufacturer of the components. These manufacture supplied models may be used as inputs to the remaining life prediction tool.

For example, a turbine manufacturer may have an electronic library of dovetail designs. The software tool 26 may receive an identifying input for a particular dovetail design that causes the tool to access the library and download a geometrical electronic model of the dovetail or other information that define the geometrical dimensions of the dovetail. With the information regarding the geometry of the dovetail, the tool 26 may automatically generate a FE mesh model of the dovetail and determines the loads applied to the hooks of the dovetail. The tool 26 applies the crack information 30 to the dovetail geometry so that the FE mesh model accounts for the effects of cracks in the hooks. Knowing the loads on the hooks, deterministic analyses are performed (see FIGS. 4 and 5) to evaluate whether the dovetail has reached a failure criteria 32. To predict remaining life of the dovetail using the deterministic analyses, the size (e.g., depth and/or width) of the cracks (a1, a2, a3) are increased at the given propagation rate (da/dt) for a certain period of time, e.g., 1 year. The mesh mode of the dovetail geometry is adjusted to include the propagated cracks, and the FE analysis is performed to determine predicted hook loads at the end of the certain time period. The deterministic analyses are performed using on based on the predicted hook loads and propagated cracks and determinations are made as to whether a failure criteria is expected to be reached at the expiration of the certain period of time.

The exemplary failure outputs includes the crack size (a) of each crack as compared to the prescribed crack size limit ($a_{limit}$); the stress intensity factor (K) as compared to a plane strain fracture toughness ($K_{IC}$); the effective stress ($\sigma_{eff}$) as compared to a stress flow maximum ($\sigma_{flow}$), and a shear stress ($\tau$) as compared to a critical shear stress limit ($\tau_{limit}$).

In an exemplary example of the operation of the deterministic engine 27, the deterministic analysis 27 is completed for a certain time period (ti) to determine if a failure event is predicted to occur in that period. The entire deterministic analysis is then repeated by first extending the length of the cracks by the lengths predicted by the propagation rate times a certain time interval (da/dt*Δt). The geometric model of the dovetail is adjusting using the longer crack lengths, the FE analysis is preformed to calculate the hook loads at each hook, and the failure analyses (a, K, σ and τ) are evaluated for a failure limit. The deterministic analysis may be repeatedly recalculated the each successive estimated propagation of cracks.

The FE analysis predicts the hook loads based on the hook geometry, the cracks in the hooks and operating conditions in the wheel, such as rotational speed. As a crack propagates, it opens and slightly deforms a hook such that the hook adsorbs less of the centrifugal force applied by a turbine bucket. The geometric model of the dovetail is adjusted to include the crack data and the FE analysis accounts for the weakening of the cracked hooks.

The deterministic engine 27 predicts a time to failure for given inputs 28, 30, but may not account for other load variances due to materials, crack propagation rates and loads that occurs from one turbine wheel application to another. These other load variances can affect actual crack propagation rates, loading of the dovetail connector, and other conditions that occur during turbine operation that influence dovetail failure. To account for these variances, a probabilistic engine 34 in the software tool applies statistical distributions of conditions to the crack data (distributions a1, a2 and a3–36) and distribution for crack propagation data (da/dt 38) of the inputs to the deterministic engine 27. The output of the probabilistic engine 34 (which encompasses the deterministic engine) may be distributions of shear stress 40 ($\tau$), flow stress ($\sigma_{eff}$) 42 and stress intensity factor (K) 44. These distributions are compared to distribution of corresponding distributions of failure limits 46 for critical shear stress ($\tau_{limit}$), flow stress ($\sigma_{flow}$) and the plane strain fracture toughness ($K_{IC}$)—collectively 46.

The ranges of the distributions 40, 42 and 44 gradually creep towards their limits 46 as time periods (dt) successively progress. These ranges of distribution are compared after each iteration of the deterministic and probabilistic analyses to evaluate the overlap of the predicted distributions 40, 42, 44 to the distribution of failure limits 46 (see overlap of distribution for $\sigma_{eff}$ and $\sigma_{flow}$). such as by utilizing a Monte Carlo approach, the probabilistic engine analyzes many potential situations of initial crack size, growth rate, and material structural capacity, etc. to establish a statistical distribution in the failure time of the condition reported by ultrasonic inspection. As shown in FIG. 3, probability charts show the increase in probability with time as the failure modes begin to overlap with the failure limits for each mode.

The probabilistic engine utilizes the deterministic engine to solve for the shear stress, stress intensity, and plastic flow stresses at specific combinations of crack sizes in the dovetail geometry. These solutions are merged into a design space which can be interpolated to find the shear stress, stress intensity and plastic flow stress for any size and combination of crack flaws on a dovetail. For example, a Monte Carlo analysis is generated by using pairings of initial conditions based on known distributions for growth rate of SCC flaws, material properties, and actual crack size given a reported ultrasonic size.

The probabilistic engine may also factor in the potential for false ultrasonic indications, and cracks not seen by the ultrasonic inspection. Each of these initial conditions is analyzed to determine the time of failure. Determination of failure includes interaction between all of the deterministic failure modes preciously described and includes cascading failure, where failure of one hook in the dovetail causes overload of remaining hooks. Following calculation of failure time for the initial conditions, standard statistical techniques are used to determine a probabilistic cumulative probability of failure as a function of time.

Figure 4:
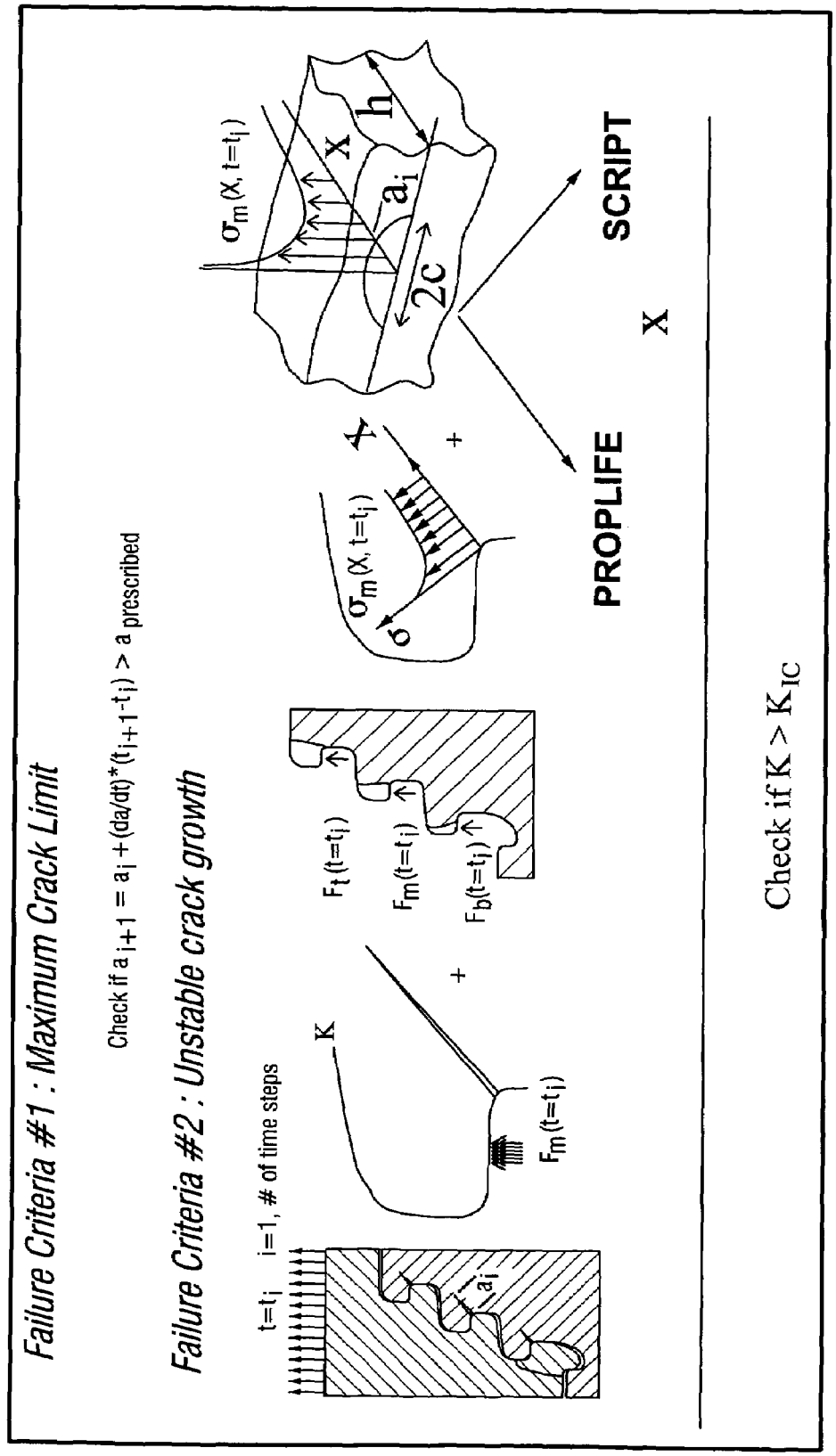
FIG. 4 is a diagram illustrating a deterministic analysis of dovetail connector failure criteria for maximum crack limit and unstable crack growth.

FIG. 4 is a diagram that illustrates two failure criteria that may be modeled in the deterministic portion of the software tool. With respect to failure criteria number one, a maximum crack limit is evaluated to determine when a crack in the dovetail connector is expected to reach a maximum crack length. By applying failure criteria number, the software tool evaluates each crack and predicts when the crack will reach a prescribed crack length limit ($A_{prescribed}$) based on the expected crack propagation rate (da/dt). The software engine may evaluate the crack length$_a$ (at each successive point in time (t=i)) by adding the crack length at a prior point and time to the expected crack propagation rate for the period between each successive time period. The time until a crack in a dovetail connector reaches a crack limit is a time to failure.

In failure criteria two, the deterministic engine of the software tool evaluates unstable crack growth by analyzing the stress concentration (K) at each crack. In particular, engine calculates the stress normal to the crack surface from the hook load applied to a particular hook. Based on this stress and the crack geometry the stress intensity factor is determined. A failure is determined to occur when the stress concentration rises to the plane strain fracture toughness level ($K_{IC}$).

Figure 5:
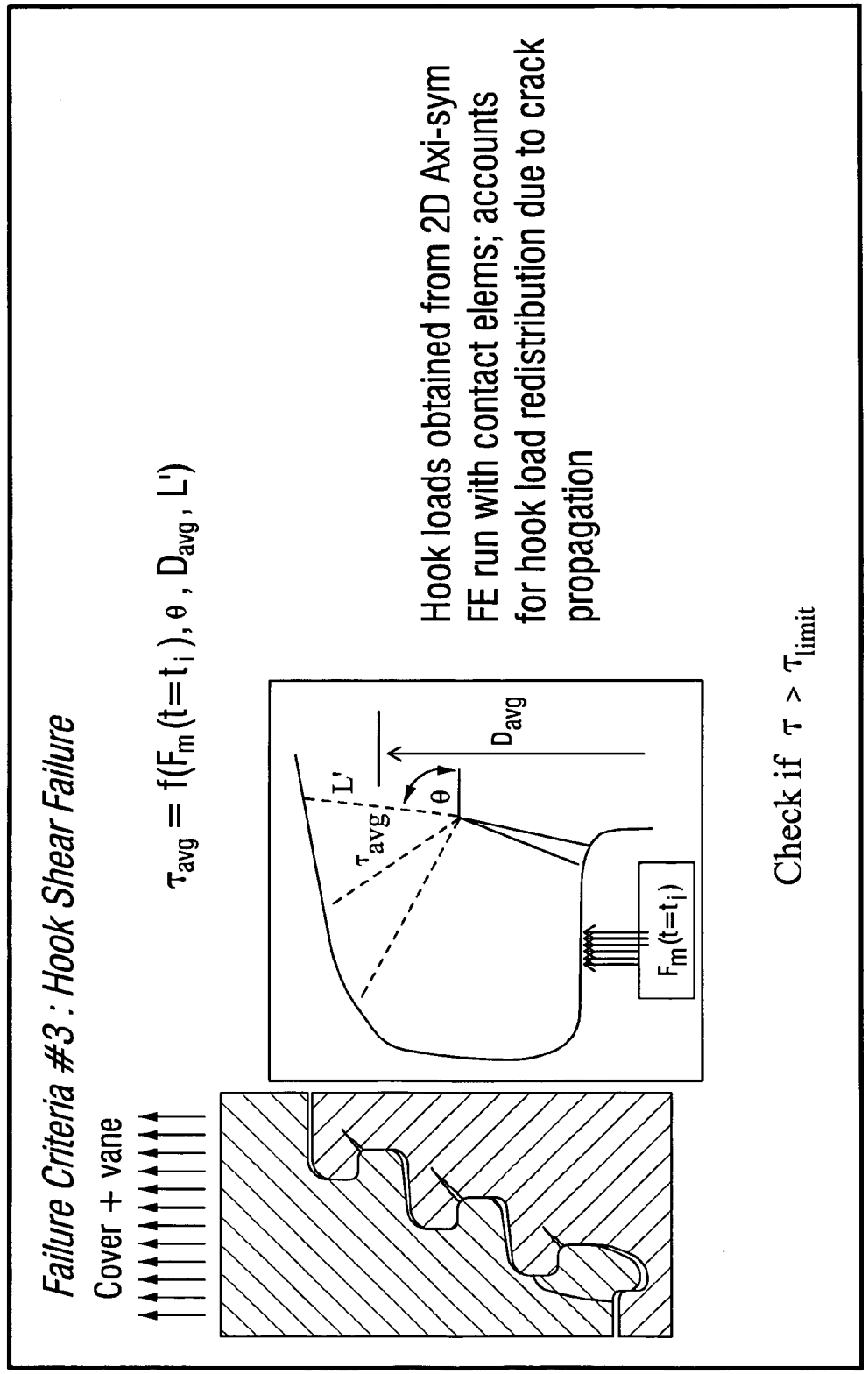
FIG. 5 is a diagram illustrating a dovetail connector failure criteria based on hook shear failure.

FIG. 5 is a diagram illustrated a hook shear failure criteria mode. The deterministic engine may apply a hook shear failure mode to determine a time to failure based on a shear stress failure. For a given crack combination, the engine calculates the hook loads at each hook. Then for each hook, shear stress over the areas defined by lines drawn from the crack tip to the hook boundary at different angles. Then the maximum shear stress is chosen to be compared with the critical shear stress limit. Other failure criteria may be applied by the deterministic engine, such as applying plastic limit load analysis to determine if a plastic limit load of a hook is exceeded. The deterministic engine may apply one or more of the tools for determining failure described in FIGS. 4 and 5.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for predicting a remaining operational life of a turbine component comprising:

obtaining crack flaw data regarding current crack flaws in the turbine component;

using the crack flaw data with data regarding a structure and operating conditions of the turbine component to determine force loads applied to the turbine component and generate crack propagation data, applying a probalistic analysis to the crack flaw data and the generated crack propagation data to generate a statistical distribution of crack data, applying the statistical distribution of crack data to predict a time to failure of the component by iteratively determining the force loads for successive periods of time, and outputting to a user an indicator of the predicted time to failure.

2. The method of claim 1 wherein the turbine component is a turbine rotor having a peripheral dovetail connector, and said crack flaw data represents crack flaws in the dovetail connector.

3. The method of claim 1 wherein the crack flaw data is obtained by an ultrasonic inspection of surfaces of the turbine component.

4. The method of claim 2 wherein the crack flaw data is obtained by an ultrasonic inspection of hooks in the dovetail connector.

5. The method of claim 1 wherein the data regarding the structure of the turbine component is mathematical model of the turbine component generated by a manufacturer of the component.

6. The method of claim 1 wherein the iterative determination of force loads and crack propagation includes determining loads applied to a plurality of load bearing positions on the component, determining crack propagation due to a period of operation, determining deformation of the load bearing positions due to the propagated crack.

7. The method of claim 6 wherein the determinations of load, propagation and deformation are performed repeatedly to determine the predicted time to failure.

8. A method for predicting a remaining operational life of a turbine component comprising:
   a. obtaining crack flaw data regarding a current crack flaw in the turbine component and an expected propagation rate for the crack flaw;
   b. applying a probalistic analysis to the crack flaw data and expected crack propagation rate to generate statistical distribution of the propagation of the crack flaw during a predetermined operating time period of the component;
   c. using the statistical distribution of the propagated crack flaw and data regarding a structure of the turbine component to determine a load applied to the turbine component during the predetermined operating time period of the component;
   d. determining whether the turbine component at the end of the predetermined operating time period has reached a crack failure criteria based on the statistical distribution of the propagated crack flaw and the determined load, and
   e. generating an indicator of a predicted remaining life of the component, wherein the indicator is understandable by a user.

9. The method of claim 8 further comprising repeating steps b to d for successive periods of predetermined operating time periods to determine the predicted remaining life of the component.

10. The method of claim 8 wherein the turbine component is a turbine rotor having a peripheral dovetail connector, and said crack flaw data represents crack flaws in the dovetail connector.

11. The method of claim 8 wherein the crack flaw data is obtained by an ultrasonic inspection of surfaces of the turbine component.

12. The method of claim 11 wherein the crack flaw data is obtained by an ultrasonic inspection of hooks in the dovetail connector.

13. The method of claim 8 wherein the data regarding the structure of the turbine component is a mathematical model of the turbine component.

14. The method of claim 8 wherein the iterative determination of force loads and crack propagation includes determining loads applied to a plurality of load bearing positions on the component, determining crack propagation due to a period of operation, determining deformation of the load bearing positions due to the propagated crack.

15. The method of claim 14 wherein the determinations of load, propagation and deformation are performed repeatedly to determine the predicted time to failure.

16. A system for predicting a remaining operational life of a turbine component comprising:
   an inspection device that collects crack flaw data regarding current crack flaws in the turbine component;
   a computer system including a processor and a data storage device, wherein the data storage device stores the crack flaw data and data regarding the structure and operation of the turbine component and a software tool comprising algorithms for analyzing the software component and predicting a remaining life of the component;
   wherein the algorithms include a probalistic analytical tool receiving as inputs the crack flaw data and outputting a statistical distribution of crack data, and
   using the statistical distribution of crack flaw data and the data regarding the structure and operation of the turbine component to determine statistical distributions of force loads applied to the turbine component and statistical distributions of crack propagation resulting from the force loads, wherein the determination of force loads and crack propagation is performed iteratively to predict a time to failure of the component, and
   outputting to a user an indicator of the predicted time to failure.

17. The system of claim 16 wherein the turbine component is a turbine rotor having a peripheral dovetail connector, and said crack flaw data represents crack flaws in the dovetail connector.

18. The system of claim 16 wherein the inspection device is an ultrasonic device that inspects surfaces of the turbine component.

19. The system of claim 18 wherein the crack flaw data is obtained by an ultrasonic inspection of hooks in the dovetail connector.

20. The system of claim 16 wherein the data regarding the structure of the turbine component is a mathematical model of the turbine component.

* * * * *